(12) United States Patent
Reynard et al.

(10) Patent No.: US 11,961,238 B2
(45) Date of Patent: Apr. 16, 2024

(54) TOOTH SEGMENTATION USING TOOTH REGISTRATION

(71) Applicant: TROPHY SAS, Marne la Vallee (FR)

(72) Inventors: Delphine Reynard, Montreuil (FR); Xavier Ripoche, Marne la Vallee (FR); Yannick Glinec, Serris (FR); Jean-Pascal Jacob, Marne la Vallee (FR); Pascal Narcisse, Marne la Vallee (FR); Sabrina Capron-Richard, Noisiel (FR); Aude Lagardere, Paris (FR)

(73) Assignee: Nobel Biocare Services AG, Kloten (CH)

( * ) Notice: Subject to any disclaimer, the term of this patent is extended or adjusted under 35 U.S.C. 154(b) by 403 days.

(21) Appl. No.: 17/418,634

(22) PCT Filed: Dec. 27, 2019

(86) PCT No.: PCT/EP2019/087083
§ 371 (c)(1),
(2) Date: Jun. 25, 2021

(87) PCT Pub. No.: WO2020/136243
PCT Pub. Date: Jul. 2, 2020

(65) Prior Publication Data
US 2022/0122264 A1    Apr. 21, 2022

(30) Foreign Application Priority Data
Dec. 28, 2018   (FR) .................................. 18306870.9

(51) Int. Cl.
G06T 7/12   (2017.01)
A61B 6/03   (2006.01)
(Continued)

(52) U.S. Cl.
CPC ................ G06T 7/12 (2017.01); A61B 6/032 (2013.01); A61B 6/145 (2013.01); A61B 6/4085 (2013.01);
(Continued)

(58) Field of Classification Search
None
See application file for complete search history.

(56) References Cited

U.S. PATENT DOCUMENTS 5,270,926 A   12/1993  Tam
5,999,587 A   12/1999  Ning et al.
(Continued)

FOREIGN PATENT DOCUMENTS

CN   108665533 A   10/2018

OTHER PUBLICATIONS

D.L. Page et al., "Perception-based 3D Triangle Mesh Segmentation Using Fast Marching Watersheds," Proc. Intl. Conf. on Computer Vision and Pattern Recognition, II:27-32, (Jun. 2003).
(Continued)

*Primary Examiner* — Leon Flores
(74) *Attorney, Agent, or Firm* — Alston & Bird LLP

(57) ABSTRACT

A method for segmenting a 3D model image of a patient's dentition obtains a first 3D model image of the patient dentition and obtains a first segmentation of the first 3D model image, wherein the first segmentation provides at least a tooth surface contour and a tooth label for one or more teeth of the first 3D model. A second 3D model image of the patient dentition is obtained. Each segmented tooth surface contour of the first 3D model is registered to corresponding tooth surface contour of the second 3D model. A second segmentation of the second 3D model image is obtained according to the registered tooth surface contour, wherein the second segmentation similarly pro-
(Continued)

vides at least tooth surface contour and a tooth labeling for one or more teeth of the second 3D model image. The segmented second 3D model image is displayed, transmitted, or stored.

15 Claims, 9 Drawing Sheets

(51) Int. Cl.
A61B 6/14 (2006.01)
A61B 6/40 (2024.01)
A61C 7/00 (2006.01)
G06T 7/00 (2017.01)
G06T 7/33 (2017.01)

(52) U.S. Cl.
CPC ............ *A61C 7/002* (2013.01); *G06T 7/0012* (2013.01); *G06T 7/344* (2017.01); *A61C 2007/004* (2013.01); *G06T 2207/10081* (2013.01); *G06T 2207/30036* (2013.01)

(56) References Cited

U.S. PATENT DOCUMENTS

| | | | |
|---|---|---|---|
| 8,416,984 | B2 | 4/2013 | Liang et al. |
| 8,670,521 | B2 | 3/2014 | Bothorel et al. |
| 2003/0039389 | A1 | 2/2003 | Jones et al. |
| 2013/0120532 | A1 | 5/2013 | Milch |
| 2013/0120533 | A1 | 5/2013 | Milch |
| 2014/0169648 | A1* | 6/2014 | Andreiko ................ G16Z 99/00 382/128 |
| 2014/0227655 | A1* | 8/2014 | Andreiko ............. A61B 6/5211 433/29 |
| 2015/0305830 | A1 | 10/2015 | Howard et al. |
| 2016/0004811 | A1 | 1/2016 | Somasundaram et al. |
| 2018/0005371 | A1 | 1/2018 | Sabina et al. |

OTHER PUBLICATIONS

European Search Report and Search Opinion received for EP Application No. 18306870.9, dated Jun. 4, 2019, 9 pages.
H. Akhoondali et al., "Rapid Automatic Segmentation and Visualization of Teeth in CT-Scan Data," Journal of Applied Sciences, 9(11):2031-2044, (2009).
International Preliminary Report on Patentability received for PCT Patent Application No. PCT/EP2019/087083, dated Jul. 8, 2021, 9 pages.
International Search Report and Written Opinion received for PCT Patent Application No. PCT/EP2019/087083, dated Feb. 7, 2020, 11 pages.
Joe Min Moon, "Evaluation of Software Developed for Automated Segmentation of Digital Dental Models," Thesis, 58 pages, (Feb. 2012).
Office Action received for European Application No. 18306870.9, dated Jul. 11, 2022, 4 pages.
Office Action received for European Application No. 18306870.9, dated Jun. 23, 2021, 3 pages.
Radu Rusu, "Semantic 3D Object Maps for Everyday Manipulation in Human Living Environments," Dissertation, 284 pages, (Aug. 17, 2009).
Thomas Kronfeld et al., "Snake-Based Segmentation of Teeth from Virtual Dental Casts," Computer-Aided Design & Applications, 7(a):1-12, (2010).

\* cited by examiner

TOOTH SEGMENTATION USING TOOTH REGISTRATION

TECHNICAL FIELD

The disclosure relates generally to dental imaging and more particularly relates to methods and apparatus for segmentation of intraoral features.

BACKGROUND

Optical intraoral scans produce contours of dentition objects and have been helpful in improving visualization of teeth, gums, and other intra-oral structures. Surface contour information can be particularly useful for assessment of tooth condition and has recognized value for various types of dental procedures, such as for restorative dentistry. This can provide a valuable tool to assist the dental practitioner in identifying various problems and in validating other measurements and observations related to the patient's teeth and supporting structures. Surface contour information can also be used to generate 3D models of dentition components such as individual teeth; the position and orientation information related to individual teeth can then be used in assessing orthodontic treatment progress.

For orthodontic and other restorative procedures, a model of patient dentition is generated, initially and at various stages of the process, using surface contour information that can be acquired from an intraoral scanner. The model can be formed as a point cloud or mesh formed from scanned image content showing the surface contour. A number of standardized metrics can then be applied to the models for comparison and to track overall progress of the treatment regimen.

One part of the process for analyzing and using the model is tooth segmentation. Segmentation enables the individual tooth to be identified from within the model and its features and allows its orientation to be correctly analyzed as part of the treatment evaluation. At a minimum, segmentation defines the tooth at each position in the model, such as along the point cloud or mesh, and identifies the tooth label. Segmentation may also identify features such as the cervical limit and the tooth cusp and fossae. Segmentation can also provide needed information for determining the tooth axis (mesio-distal and main axis). For example, segmentation allows the practitioner to identify and isolate the crown and to distinguish other visible portions of the tooth from gums and related supporting structure.

Conventional segmentation techniques can be time-consuming and can often require manual intervention in order to correct errors or to resolve ambiguities in results. The need to repeat segmentation processing each time a model is generated for a patient, such as at various intervals during an ongoing procedure, adds time and cost to the overall process and can make it difficult to properly evaluate treatment progress.

SUMMARY

An object of the present disclosure is to address the need for improved tooth segmentation and workflow in restorative and orthodontic imaging. Embodiments of the present disclosure support segmentation processing with the additional leverage available from the overall treatment plan and from previous segmentation results.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to one aspect of the disclosure, there is provided a method for segmenting a 3D model image of a patient's dentition comprising:

a) obtaining a first 3D model image of the patient dentition and obtaining a segmentation of the first 3D model image, wherein the first segmentation provides at least a tooth surface contour and a tooth label for one or more teeth of the first 3D model image;

b) obtaining a second 3D model image of the patient dentition, the second 3D model image having a surface;

c) registering one or more segmented tooth surface contours of the first 3D model image to the surface of the second 3D model image;

d) obtaining a second segmentation of the second 3D model image according to the registered tooth surface contours, wherein the second segmentation similarly provides at least tooth surface contour and tooth labeling for one or more teeth of the second 3D model image; and e) storing the segmented second 3D model image.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE EMBODIMENTS

Figure 1:
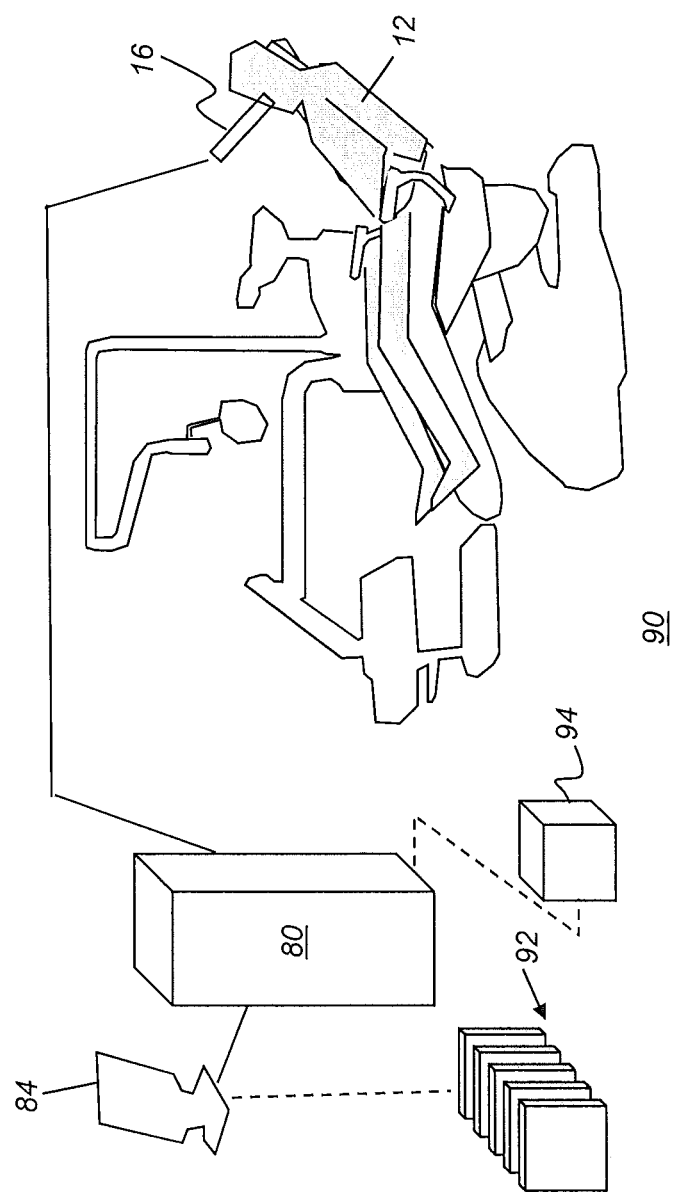
FIG. 1 is a schematic diagram that shows a surface contour imaging apparatus for obtaining a 3D view from a succession of reflectance images according to an embodiment of the present disclosure.

The following is a detailed description of the preferred embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise. In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a scanner or by using a computer mouse or by touch screen or keyboard entry.

In the context of the present disclosure, the term "subject" is generally used to denote the patient who is imaged as the "object" of an optical system. The terms "subject" and "object" can thus be used interchangeably when referring to the imaged patient. The subject or object could alternately be a dental impression or a cast or other model obtained from the dental impression.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

Mesh representation can be provided using either 3D volume radiographic methods such as CBCT or structured light and other reflectance imaging methods using an intraoral scanner, or by using some combination of radiographic and reflection imaging.

The terms "3D model", "model", "model image", "3D model image", "point cloud", "3D mesh", and "mesh" may be used synonymously in the context of the present disclosure for image structures that visually represent the 3D surface contour of imaged teeth. A dense point cloud is formed using techniques familiar to those skilled in the volume imaging arts for surface contour representation and relates generally to methods that identify points in space corresponding to surface features. A dense point cloud can be generated, for example, using the reconstructed contour data from one or more reflectance images. A mesh can be generated using the same acquired surface contour to identify vertices that serve as the basis for a polygon model for tooth and gum surfaces. The mesh and point cloud representations for a 3D surface can have the same visual appearance depending on magnification; computed coordinates for vertices of the mesh and particular points in the point cloud, however, need not be identical.

CBCT apparatus can be used for acquiring 3D volume content usable for generating a 3D model image of patient dentition. As is well known to those skilled in the imaging arts, the CBCT apparatus rotates an x-ray source and a detector about the subject and acquires a set having a series of radiographic 2D projection images at different angles about the subject. Reconstruction processes are then used to faun a reconstructed 3D volume image of the subject or the object using the set of 2D projection images.

Reference is hereby made to commonly assigned U.S. Pat. No. 8,670,521 entitled "Method for Generating an Intraoral Volume Image" to Bothorel et al. for more detailed information on how the CBCT apparatus operates. For forming a model according to an embodiment of the present disclosure, the CBCT apparatus is typically employed to scan a mold or imprint of patient dentition.

CBCT imaging apparatus and the imaging algorithms used to obtain 3D volume images using such systems are well known in the diagnostic imaging art and are, therefore, not described in detail in the present application. Some exemplary algorithms and approaches for forming 3D volume images from the 2D projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat. No. 5,270,926 entitled "Method and Apparatus for Reconstructing a Three-Dimensional Computerized Tomography (CT) Image of an Object from Incomplete Cone Beam Data" to Tam.

In typical applications, a computer or other type of dedicated logic processor can act as control logic processor for obtaining, processing, and storing image data as part of the CBCT system, along with one or more displays for viewing image results. As noted previously, the acquired 3D volume from the CBCT system can be used for generating a model of patient dentition, which may be in the form of a mesh or point cloud, as described subsequently in more detail.

The schematic diagram of FIG. 1 shows a surface contour imaging apparatus 90 that can be used for obtaining 3D content for model generation from a succession of reflectance images according to an embodiment of the present disclosure. An imaging device 16, typically a hand-held digital camera, a color depth camera, handheld 3D scanner, or intra-oral 3D scanner, is scanned through the mouth of patient 12 for acquiring a set having multiple reflectance images and associated depth information. A control logic processor 80, configurable to execute programmed instructions, is in signal communication with imaging device 16 and a display 84. Processor 80 obtains image data from imaging device 16 and processes this image data along with depth information in order to generate individual 3D views 92. Control logic processor 80 then combines the scanned 3D views in order to generate, store, and optionally render, on display 84, a composite 3D model surface 94.

Figure 2:
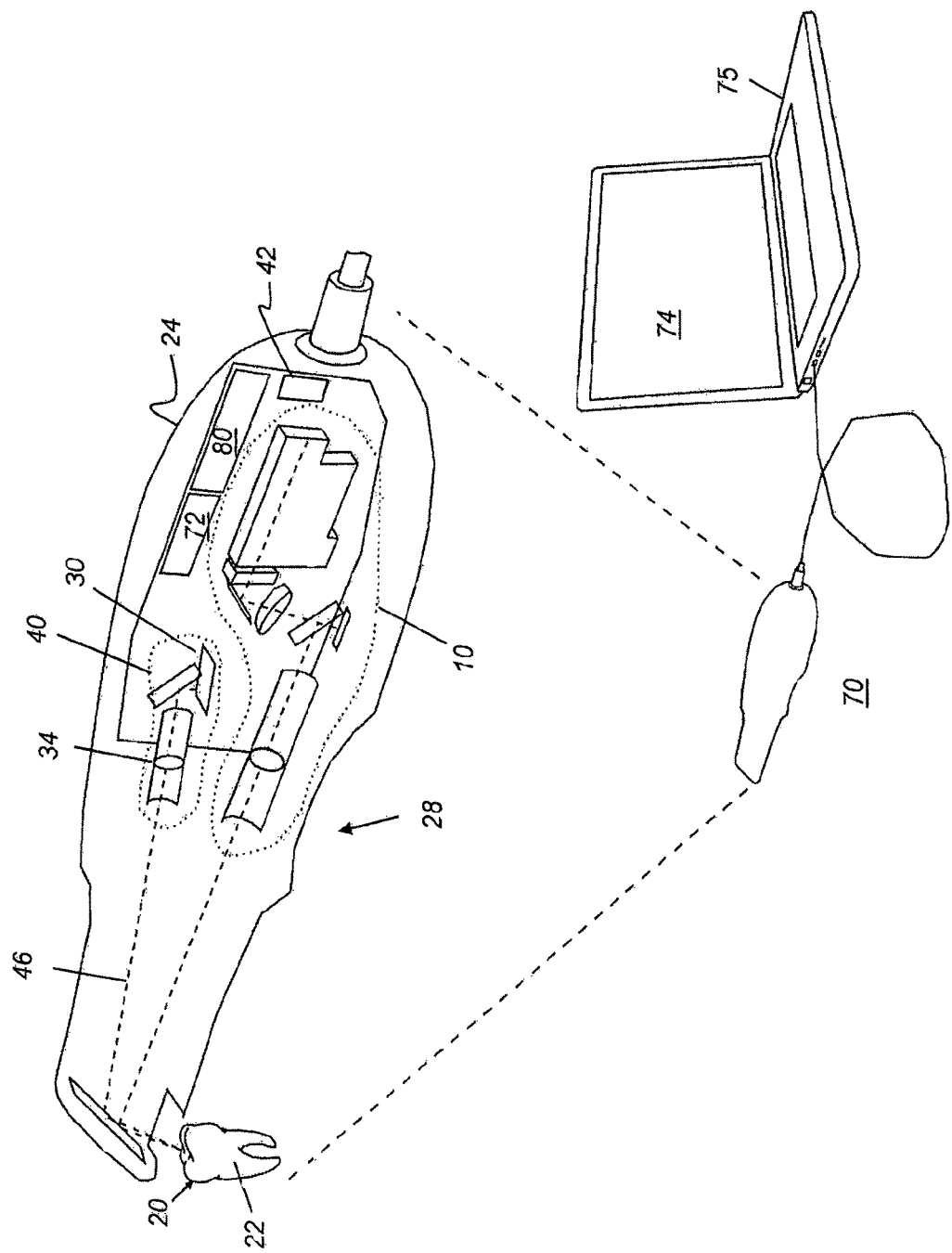
FIG. 2 is a schematic diagram showing an imaging apparatus that can operate as a video camera for polychromatic reflectance image data capture as well as a scanner for executing related projecting and imaging functions.

FIG. 2 is a schematic diagram showing an imaging apparatus 70 that can operate as a video camera 24 for polychromatic reflectance image data capture as well as a scanner 28 for executing related projecting and imaging functions used to characterize surface contour with structured light patterns 46. A handheld imaging apparatus 70 uses a video camera 24 for image acquisition for both contour scanning and image capture functions according to an embodiment of the present disclosure. Control logic processor 80, or other type of computer that may be part of camera 24, controls the operation of an illumination array 10 that generates the structured light and directs the light toward a surface position and controls operation of an imaging sensor array 30. Image data from surface 20, such as from a tooth 22, is obtained from imaging sensor array 30 and stored as video image data in a memory 72. Imaging sensor array 30 is part of a sensing apparatus 40 that includes an objective lens 34 and associated elements for acquiring video image content. Control logic processor 80, in signal communication with camera 24 components that acquire the image, processes the received image data and stores the mapping in memory 72. The resulting image from memory 72 is then optionally rendered and displayed on a display 74, which may be part of another computer 75 used for some portion of the processing described herein. Memory 72 may also include a display buffer. One or more sensors 42, such as a motion sensor, can also be provided as part of scanner 28 circuitry.

In structured light imaging, a pattern of lines or other shapes is projected from illumination array 10 toward the surface of an object from a given angle. The projected pattern from the illuminated surface position is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of structured light imaging, used in order to complete the contour mapping of the surface and to increase overall resolution in the contour image. By way of example and not limitation, use of structured light patterns for surface contour characterization is described in commonly assigned U.S. Patent Application Publications No. US2013/0120532 and No. US2013/0120533, both entitled "3D INTRAORAL MEASUREMENTS USING OPTICAL MULTILINE METHOD" and incorporated herein in their entirety.

3D Surface Image Generation as Mesh/Point Cloud

By knowing the instantaneous position of the camera and the instantaneous position of the line of light within an object-relative coordinate system when the image was acquired, a computer and software can use triangulation methods to compute the coordinates of numerous illuminated surface points relative to a plane. As the plane is moved to intersect eventually with some or all of the surface of the object, the coordinates of an increasing number of points are accumulated. As a result of this image acquisition, a point cloud of vertex points or vertices can be identified and used to represent the extent of a 3D surface within a volume. The points in the point cloud then represent actual, measured points on the three-dimensional surface of an object. A mesh can alternately be constructed, such as by connecting points on the point cloud as vertices that define individual congruent polygonal faces (typically triangular faces) that characterize the surface shape. The full 3D surface image model can then be formed by combining the surface contour information provided by the mesh with monochromatic or polychromatic image content obtained from a camera, such as camera 24 of FIG. 2.

Polychromatic image content can be provided in a number of ways, including the use of a single monochrome imaging sensor with a succession of images obtained using illumination of different primary colors, one color at a time, for example. Alternately, a color imaging sensor could be used.

Figure 3:
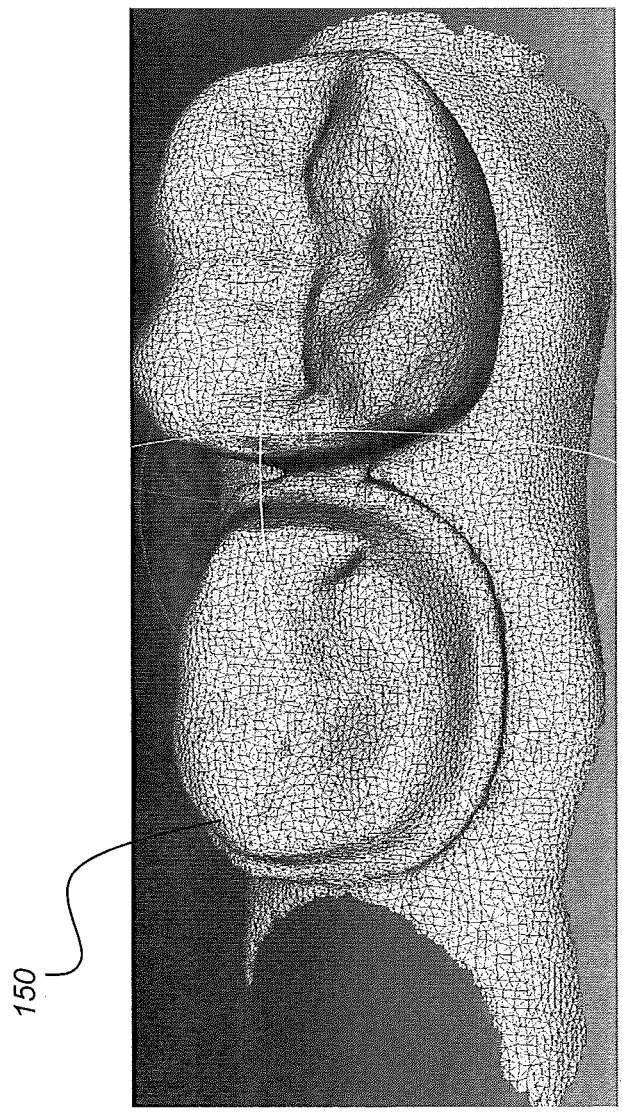
FIGS. 3 and 4 show point cloud images generated from a succession of structured light images.
Figure 4:
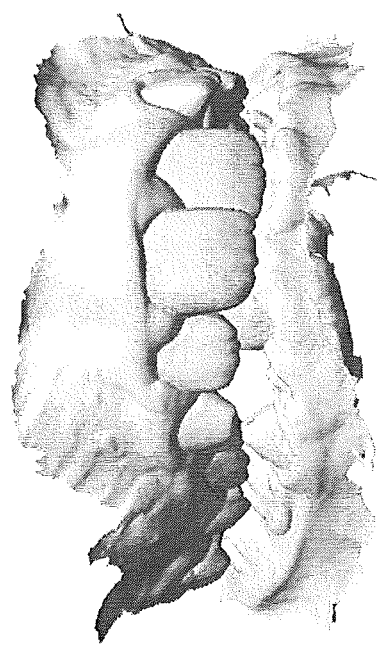

Image processing at control logic processor 80 can generate a 3D contour surface model using line scan data from structured light imaging, or using point cloud or mesh data or CBCT volume image data. By way of example, FIGS. 3 and 4 show a point cloud or mesh 150 generated from a succession of structured light images. Further processing of the point cloud content can be used to generate a mesh as an alternative contour surface model.

It should be noted that other types of reflectance imaging can be used for obtaining intraoral surface contour data used to generate the 3D surface model. Surface contour information can be obtained using time-of-flight imaging or range imaging methods, such as structure-from-motion processing, for example.

Segmentation Methods

Various approaches for addressing the segmentation problem for mesh images or other types of 3D surface images have been proposed, such as the following:

(i) A method described in the article "Snake-Based Segmentation of Teeth from Virtual Dental Casts" by Thomas Kronfeld et al. (in Computer-Aided Design & applications, 7(a), 2010) employs an active contour segmentation method that attempts to separate every tooth and gum surface in a single processing iteration. The approach that is described, however, is not a topology-independent method and can fail, particularly where there are missing teeth in the jaw mesh.

(ii) An article entitled "Perception-based 3D Triangle Mesh Segmentation Using Fast Marching Watershed" by Page, D. L. et al. (in *Proc. CVPI* vol II 2003) describes using a Fast Marching Watershed method for mesh segmentation. The Fast Marching Watershed method that is described requires the user to manually enter seed points. The seed points must be placed at both sides of the contours of the regions under segmentation. The method then attempts to segment all regions in one step, using seed information. For jaw mesh segmentation, this type of method segments each tooth as well as the gum at the same time. This makes the method less desirable, because segmenting teeth from the gum region typically requires parameters and processing that differ from those needed for the task of segmenting teeth from each other. Using different segmentation strategies for different types of dentition components with alternate segmentation requirements would provide better performance.

(iii) For support of his thesis, "Evaluation of software developed for automated segmentation of digital dental models", M. J. Moon used a software tool that decomposed the segmentation process into two steps: separation of teeth from gingival structure and segmentation of whole arch structure into individual tooth objects. The software tool used in Moon's thesis finds maximum curvature in the mesh and requires the user to manually choose a curvature threshold to obtain margin vertices that are used for segmenting the tooth. The software also requires the user to manually edit margins in order to remove erroneous segmentation results. Directed to analysis of shape and positional characteristics, this software tool does not consider employing color information in the separation of teeth regions from the gum regions.

(iv) U.S. Patent application 20030039389 A1 entitled "Manipulation a digital dentition model to form models of individual dentition components" by Jones, T. N. et al. disclose a method of separating portions of the dentition model representing the adjacent teeth.

Segmentation Workflow

An embodiment of the present disclosure provides an improved workflow for tooth segmentation that takes advantage of previous tooth segmentation data in order to advance and streamline the segmentation process.

Figure 5:
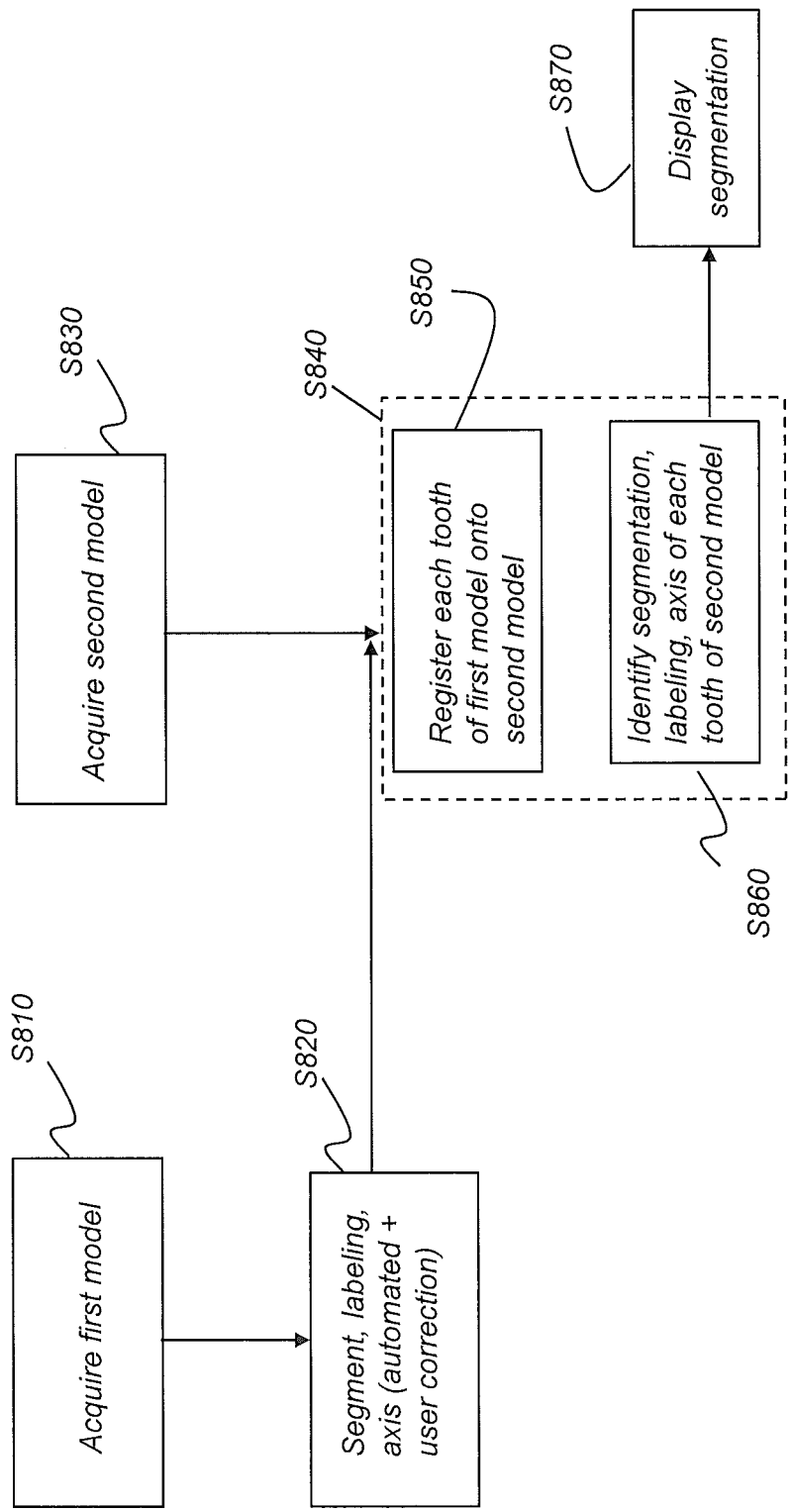
FIG. 5 is a logic flow diagram that gives an overview of the overall workflow sequence, according to an embodiment of the present disclosure.

The simplified workflow logic diagram of FIG. 5 gives an overview of the overall workflow sequence for obtaining segmentation of a 3D surface model using tooth registration. In an initial acquisition step S810, a first 3D surface model image of patient dentition is acquired. For example, the first model can be a 3D mesh virtual model initially formed prior to the beginning of patient treatment. The surface contour characterization that is obtained can be from an intraoral scanner or can be calculated from a CBCT scan of the imprint or mold of the patient dentition. Alternately, intraoral scanner and CBCT information can be combined to obtain the surface contour for the 3D model image.

An initial segmentation step S820 is performed on the first 3D model image and the resulting segmentation data are stored for subsequent use. Initial segmentation step S820 provides segmentation of the individual teeth from the first 3D model image, along with tooth labeling and axis information as determined from the tooth crown. Using the 3D mesh or other surface contour model, a significant number of features can be identified for each tooth as part of segmentation, including axis (Mesio-distal, vestibule-lingual, main axis), cusps, fossae, and largest contour, cervical limit for example.

Other reference for tooth segmentation is hereby made to the following:

Akhoondali et al. in "Rapid Automatic Segmentation and Visualization of Teeth in CT-Scan Data", *Journal of Applied Sciences*, pp 2031-2044, (2009); and Gao et al. in "Tooth Region Separation for Dental CT Images", *Proceedings of the 2008 Third International Conference on Convergence and Hybrid Information Technology*, pp 897-901, (2008)

A subsequent acquisition step S830 executes, acquiring a second 3D model image, a 3D virtual model showing the surface as a mesh or point cloud with an updated surface contour characterization of the patient. A registration process S840 then takes, as input, the initial tooth segmentation of step S820 and the second 3D model data from step S830 for streamlined segmentation processing. An intra-model registration step S850 executes, coarsely registering key features of the first 3D model image to the second 3D model image, then registering each tooth of the first 3D model image to the surface of the second 3D model image. Leveraged segmentation step S860 then takes the registration information from step S850 and performs segmentation, providing labeling and axis information for each tooth of the second model 3D image corresponding to each segmented tooth of the first 3D model image. Optionally, a display step S870 then displays the segmented content. The segmented content may further or alternatively be transmitted.

Figure 6:
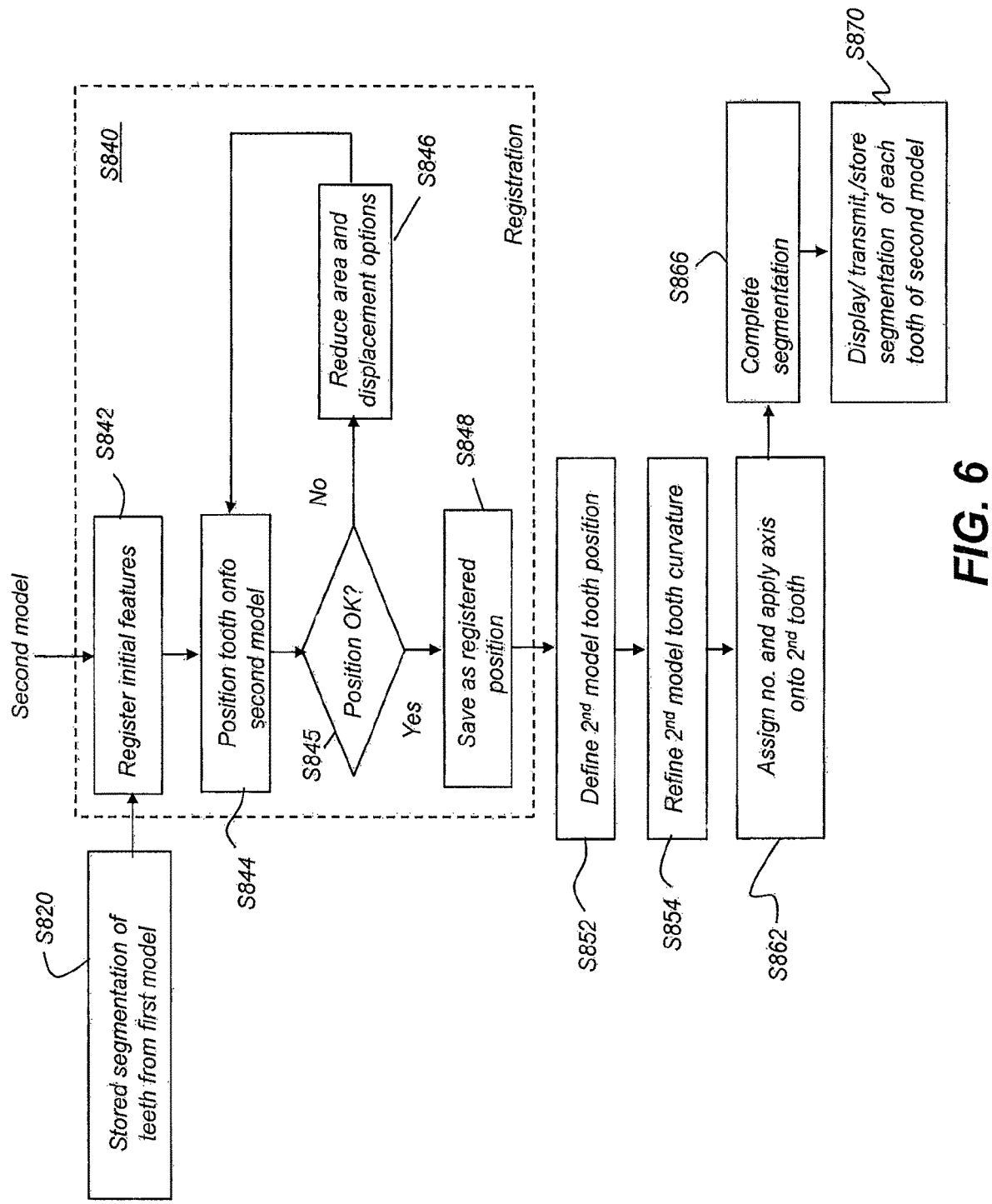
FIG. 6 is a logic flow diagram that expands upon and supplements the sequence for registration process from FIG. 5.

The logic flow diagram of FIG. 6 expands upon and supplements the sequence for registration process S840 from FIG. 5. Taking the result of initial segmentation step S820 and the second 3D model image from acquisition step S830, an initial features registration step S842 registers particular features of the second model with the initial segmentation results. For example, segmented molars from the first 3D model image can be positionally registered with the molars from the second model. Registration of the molars from the first segmented model to the volume acquired in the second scan can be generally straightforward since molar position is typically unchanged for an orthodontic treatment. Registration can use any of a number of image matching methods, such as ICP (iterative closest point) techniques.

Following initial features registration step S842 in FIG. 6, a tooth position step S844 performs additional tooth positioning to find the best position of a tooth onto the second 3D model image.

A Feature Matching Algorithm can be used for this function. According to an embodiment of the present disclosure, feature matching begins with molars, proceeding tooth by tooth to match individual features using appropriate feature-matching algorithms, familiar to those skilled in the imaging arts.

Feature Matching Algorithm

Normal information for each point of the surface contour can be estimated using well-known techniques in computer graphics, such as those described, for example, at the pointclouds.org website under documentation/tutorials/normal_estimation.php. At a query point, a local neighborhood of points is defined. The covariance matrix is computed using the local neighborhood of points. The covariance matrix C has the form:

$$C = \frac{1}{k}\sum_{i=1}^{k} \cdot (p_i - \bar{p}) \cdot (p_i - \bar{p})^T$$

wherein k is the number of points in the local neighborhood, $p_i$ values are the point coordinates and $\bar{p}$ is the average point location from the points in the local neighborhood. Superscript "T" denotes the matrix transpose.

This square, symmetric 3×3 covariance matrix can provide eigenvectors and associated eigenvalues for feature-matching computation. If a least-squares fit of the local neighborhood of points is performed using an ellipsoid, the ellipsoid axes are the eigenvectors and the axis length is related to the corresponding eigenvalues. The smallest eigenvalue of the covariance matrix represents the shortest ellipsoid axis and the associated eigenvector gives the direction of the local normal. The direction of the local normal can then be flipped if necessary to match the observation direction from the scanner. This local normal can then be assigned to the query point, which allows the computation of a surface contour with normals and colors.

The stitching procedure of the surface contour with normals and colors from the image data onto the growing surface contour has the following generic steps:

(i) Estimate one set of feature descriptors for each of the surface contour with normals and colors from the image data and for the growing surface contour. Feature descriptors for a surface contour represent a local surface description which is invariant to rigid transform (rotation/translation). For instance, the Fast Point Feature Histogram (FPFH) can be computed for each query point of the surface contour with normals. This is described, for example by Rusu, R. B., "Semantic 3D Object Maps for Everyday Manipulation in Human Living Environments", (2009, Aug. 17)). Other descriptors can be used which also include the color information from the point cloud.

(ii) Perform feature matching using both sets of feature descriptors to generate a relative placement and a score. Feature matching between a set of feature descriptors from a moving surface contour with normals onto a set of feature descriptors from a target surface contour with normals involves the generation of correspondences between feature descriptors. FPFH feature descriptors are histograms and the distance can be defined as the norm of the histogram difference between two feature descriptors. A correspondence is defined as the smallest distance from one feature descriptor onto the other set of feature descriptors. Feature matching then involves the selection of a group of correspondences to generate a relative placement. This step is typically performed using the Random Sample Consensus (RANSAC) algorithm, which consists of the random selection of three correspondences to compute a candidate relative transform and then counting the number of correspondences consistent with this candidate relative transform. A correspondence is formed of two feature descriptors, one from the moving and one from the target point cloud with normals. Each feature descriptor corresponds to a query point. A correspondence is consistent with the candidate relative transform if the moving query point, moved using the candidate relative transform, is within a predefined distance from the target query point. The candidate relative transform with the highest number of consistent correspondences becomes the final relative placement. The score indicates the quality of the final relative placement and can be the corresponding number of consistent correspondences.

(iii) Accept or reject the relative placement based on the score. The relative placement may be rejected in case the score is below a predetermined threshold. In this case, stitching is not possible and the image data are discarded.

(iv) Refine the relative placement using an iterative closest point algorithm and generate a distance measure. The refinement of the relative placement using an iterative closest point (ICP) algorithm defines point correspondences between a moved and target surface contours by finding the closest match when the relative placement is applied onto the moved surface contour. A least-square distance minimization between matches provides an update of the relative placement. The choice of point correspondences and update of the relative placement is then repeated until convergence or until a predefined number of iterations has been reached. The distance measure can be the value of the cost function used for least square distance minimization, corresponding to the final updated relative placement.

(v) Accept or reject the relative placement based on the generated distance measure. The updated relative placement can be rejected in case the distance measure is below a predetermined threshold. In this case, stitching is not possible and the image data are discarded. Otherwise, stitching is successful.

A validation step S845 tests for likelihood of positional validity, using measurements of shape and relationship to matched structures from registration step S842. Any needed adjustments can be made as necessary. If validation step S845 fails to meet pre-determined conditions for accuracy, the search area is reduced in an area reduction step S846 and tooth position step S844 repeats to attempt a repositioning over the reduced area. For example, the search area can be limited to the left or right portions of the jaw structure for subsequent reprocessing in step S844. If validation step S845 succeeds, a save registration step S848 executes, storing the registration results for the teeth. Registration results can contain a registration matrix which transforms the tooth from the first 3D model image to the second 3D model image. At this stage of processing, each tooth from the second 3D acquisition is registered to a corresponding tooth from the first model. Subsequent processing then refines tooth position and shape information in order to provide segmentation of the second model using segmentation established for the first model.

Once the stages of registration process S840 have been completed, structures of the un-segmented second 3D model image are associated with, or correlated to, corresponding segmented structures of the first model. Further refinement of the tooth shape and axis orientation in subsequent processing then helps to complete the segmentation of the second model.

Continuing with the FIG. 6 process, a positioning definition step S852 further defines tooth shape for the second model using tooth positioning results. A cervical limit refinement step S854 more accurately defines the tooth shape for each of the teeth in the second 3D model image. For each registered tooth of the second model, step S852 and S854 procedures project the cervical limit for the tooth of the first 3D model image onto the second 3D model image and optionally refine the cervical limit definition using any of a number of curvature detection techniques familiar to those skilled in the image processing art. The corresponding tooth surface contour of the second 3D model image can then be extracted using the projected cervical limit or the refined cervical limit.

To complete the segmentation processing of FIG. 6, a labeling and axis definition step S862 assigns a number or other label to the tooth from the second model and applies a registration matrix to the axis and other features (such as cusps) of the tooth of the first model, to identify the axis and other features of the tooth of the second model. This step obtains and stores the data used for segmentation of each tooth in the second model, including position, axis, and cervical limit A complete segmentation step S866 performs final segmentation processing for the second model, generating a segmented model. A display step S870 then provides display rendering, storage, or transmission of the second model segmentation.

Figure 8:
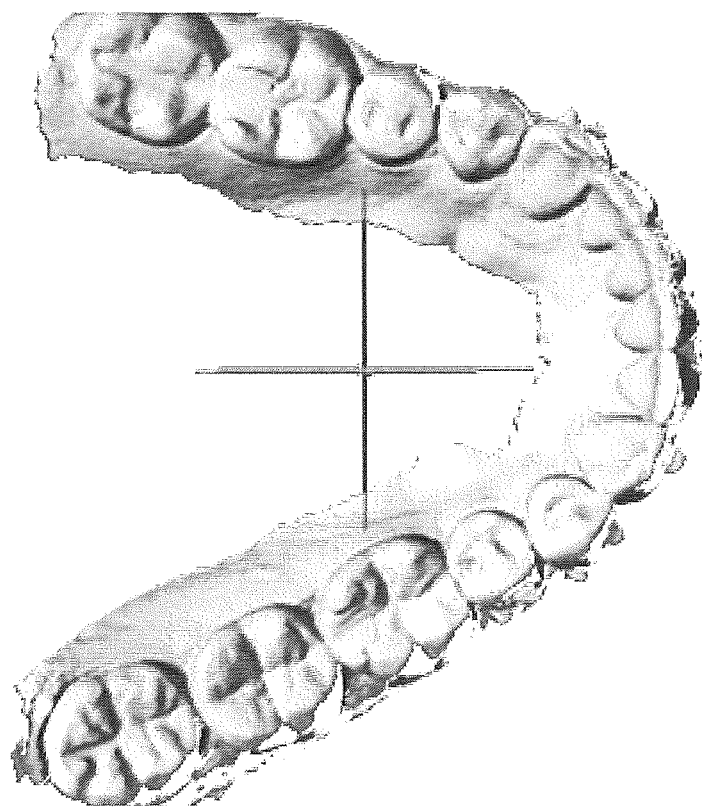
FIG. 8 shows tooth segmentation for a second model of the same dentition of FIG. 7, taken subsequently.
Figure 7:
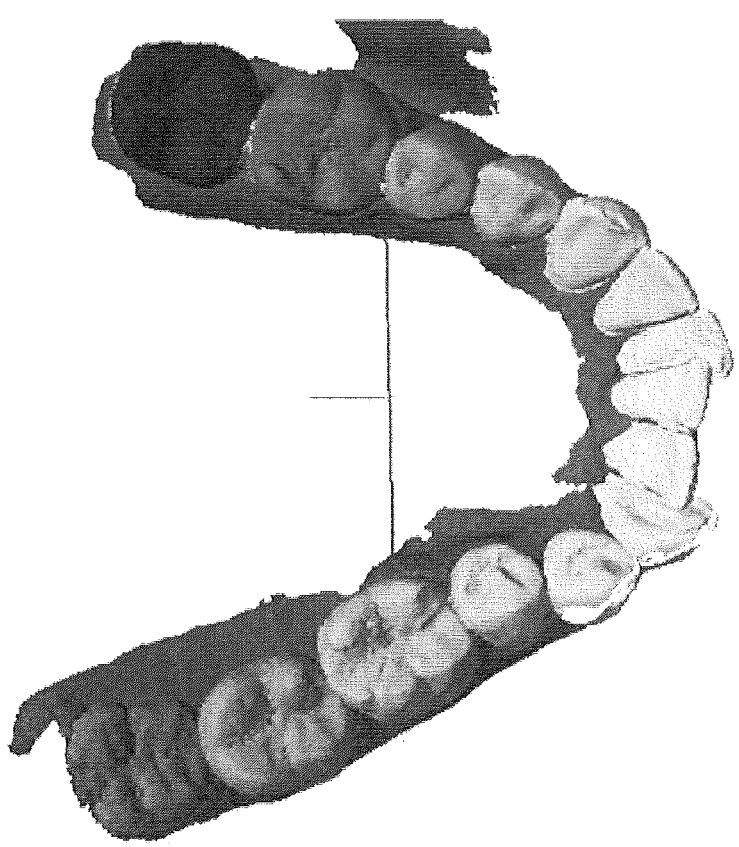
FIG. 7 shows an example of tooth segmentation from a first model of the lower jaw.

FIG. 7 shows an example of tooth segmentation from a first 3D model image of the lower jaw. FIG. 8 shows tooth segmentation for a second 3D model image of the same dentition, taken subsequently. As a result of the feature Matching algorithm, each tooth of the first model can be registered onto the second model.

Figure 9:
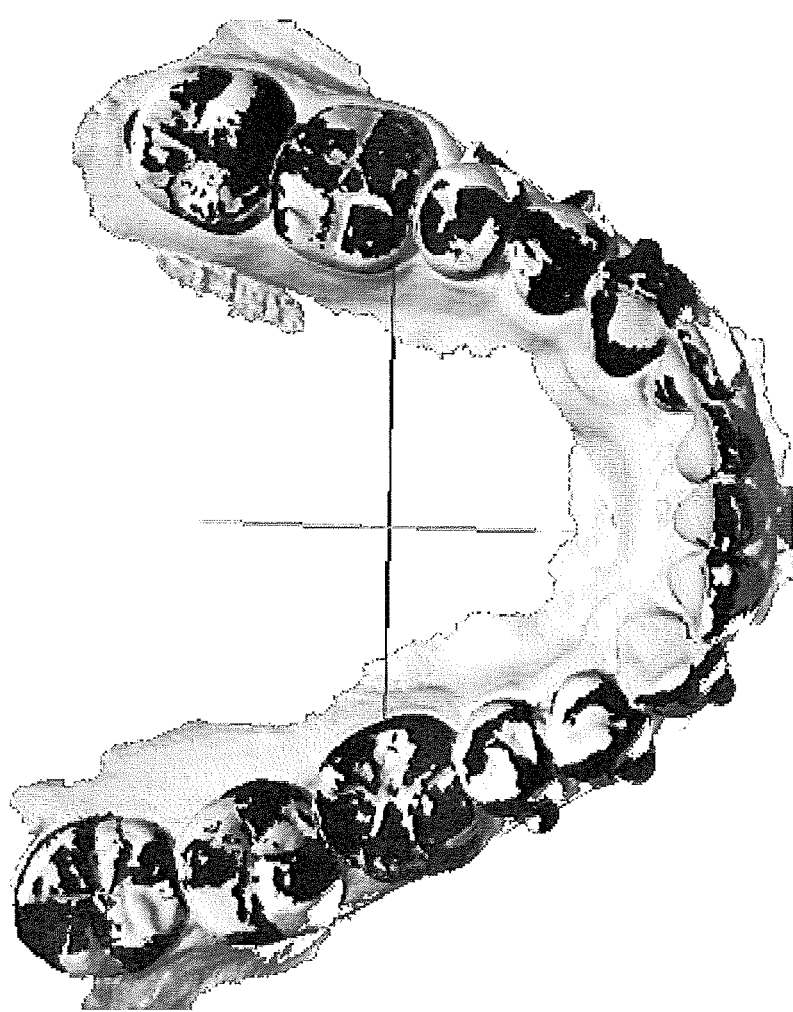
FIG. 9 shows results of feature matching for registration of the first model onto the second model.

FIG. 9 shows results of feature matching for registration of the first model onto the second model.

Figure 10:
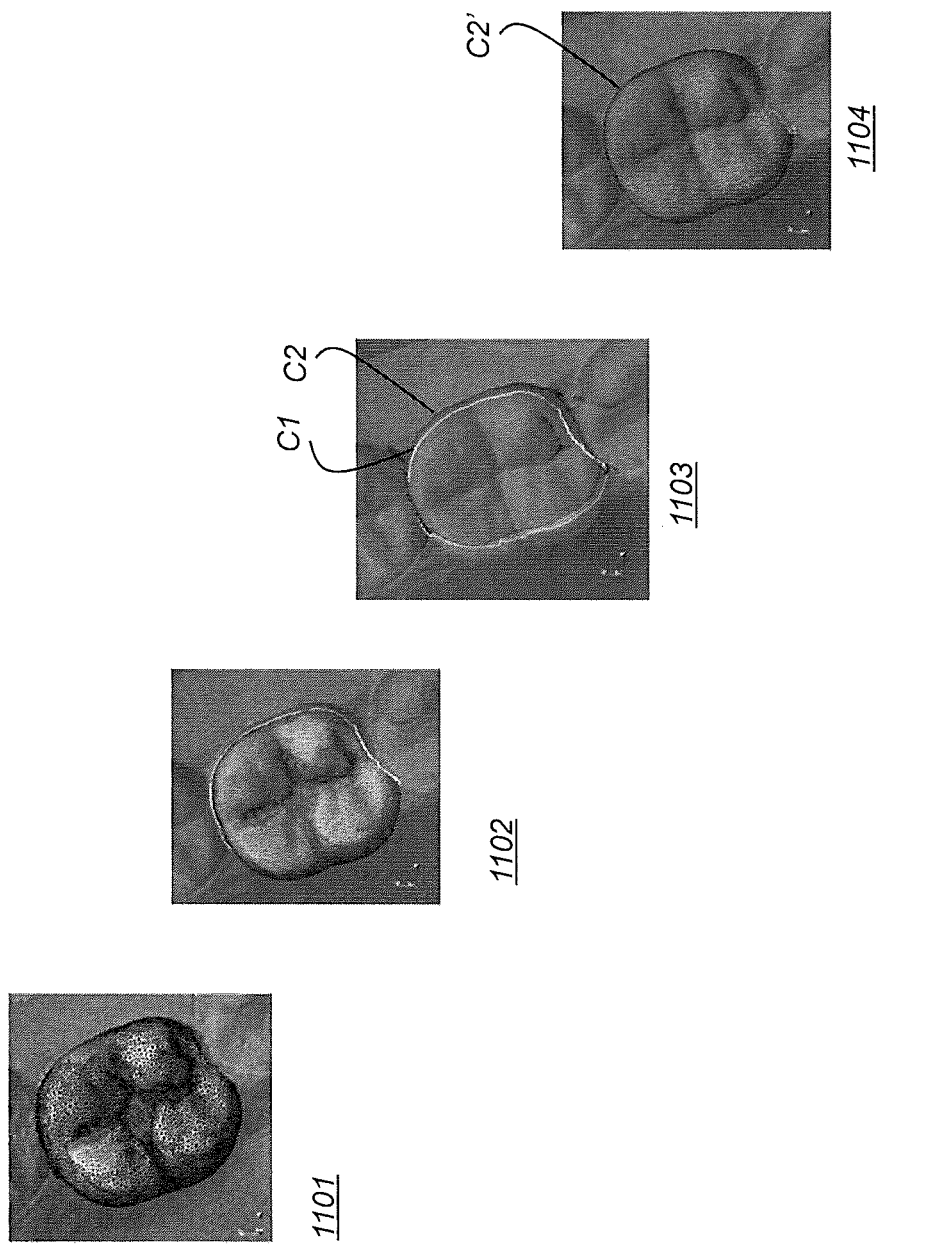
FIG. 10 illustrates processing steps using an example of a tooth according to an embodiment of the present disclosure.

FIG. 10 illustrates processing steps using an example of a single tooth (tooth 47). A FIG. 1101 shows tooth 47 segmented in the first 3D model image. A FIG. 1102 shows tooth 47 of the first model registered onto the second model. A FIG. 1103 shows cervical limits C1 and C2 detected for the first and second 3D model images, respectively, for tooth 47 (ISO numbering). Cervical limit C2 curvature is computed for the second 3D model image. A FIG. 1104 shows the refined cervical limit C2' for the second model. allowing tooth 47 to be segmented.

The invention has been described in detail with particular reference to a presently preferred embodiment, but it will be understood that variations and modifications can be effected within the spirit and scope of the invention.

The presently disclosed embodiments are therefore considered in all respects to be illustrative and not restrictive. The scope of the invention is indicated by the appended claims, and all changes that come within the meaning and range of equivalents thereof are intended to be embraced therein.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The tem' "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A method for segmenting a 3-Dimensional (3D) model image of a patient's dentition comprising:
   a) obtaining a first 3D model image of the patient dentition and obtaining a segmentation of the first 3D model image, wherein the segmentation provides at least a tooth surface contour and a tooth label for one or more teeth of the first 3D model image;
   b) obtaining a second 3D model image of the patient dentition, the second 3D model image having a surface;
   c) registering at least one segmented tooth surface contour of the first 3D model image to the surface of the second 3D model image;
   d) obtaining a second segmentation of the second 3D model image according to the registered tooth surface contours, wherein the second segmentation similarly provides at least tooth surface contour and tooth labeling for one or more teeth of the second 3D model image; and
   e) storing the segmented second 3D model image.

2. The method of claim 1 further comprising:
   f) identifying a tooth feature for at least one tooth of the first 3D model image and identifying a corresponding tooth feature of the second 3D model image based on the identified at least one tooth feature of the first 3D model image.

3. The method of claim 2 wherein the identified tooth feature for the at least one tooth of the first 3D model image comprises at least one of an axis, a cusp, or a fossa.

4. The method of claim 1 wherein obtaining the first 3D model image comprises obtaining a plurality of images from at least one of an intraoral scanner or cone beam computed tomography.

5. The method of claim 1 wherein obtaining the second 3D model image comprises obtaining a plurality of images from at least one of an intraoral scanner or cone beam computed tomography.

6. The method of claim 1 wherein obtaining the first segmentation comprises identifying a cervical limit for the at least one tooth.

7. The method of claim 6 wherein obtaining the second segmentation further comprises: (i) projecting the cervical limit for the at least one tooth of the first 3D model image onto the second 3D model image; and (ii) extracting the corresponding tooth surface contour of the second 3D model image using the projected cervical limit.

8. The method of claim 7 further comprising refining the projected cervical limit using curvature detection before the extraction step.

9. The method of claim 1 wherein registering each segmented tooth contour of the first 3D model image to corresponding contours of the second 3D model image comprises using a feature matching algorithm.

10. The method of claim 9 wherein registering segmented teeth of the first 3D model image to corresponding contours of the second 3D model image comprises defining a region of the second 3D model image wherein the feature matching algorithm is applied.

11. The method of claim 9 wherein registering each segmented tooth contour of the first 3D model image to corresponding contour of the second 3D model image further comprises registering at least one molar of the first 3D model image to corresponding features of the second 3D model image.

12. The method of claim 11 further comprising refining tooth registration using an iterative closest point algorithm.

13. A method for segmenting a 3-Dimensional (3D) model image of a patient's dentition comprising: a) obtaining a first 3D model image of the patient dentition using an intraoral scanner and generating a segmentation of the first 3D model image, wherein the segmentation provides at least a tooth surface contour and a tooth label for a plurality of teeth of the first 3D model; b) obtaining a second 3D model image of the patient dentition, the second 3D model image having a surface; c) registering each segmented tooth surface contour of the first 3D model image to the surface of the second 3D model image; d) obtaining a second segmentation of the second 3D model image according to the registered tooth surface contour, wherein the second segmentation similarly provides at least a tooth surface contour and a tooth label for a plurality of teeth of the second 3D model image; e) identifying a tooth feature for at least one tooth of the first 3D model image and identifying a corresponding tooth feature of the second 3D model image based on the identified at least one tooth feature of the first 3D model image; and f) storing the segmented second 3D model image.

14. The method of claim 13 wherein obtaining the second segmentation further comprises obtaining an axis orientation for one or more teeth of the second 3D model image.

15. An apparatus for generating a 3-Diniensional (3D) model image of a patient's dentition comprising: a) an intraoral scanner that is configured to acquire multiple images of patient dentition; b) a processor in signal communication with the intraoral scanner and configurable to execute programmed instructions for: (i) obtaining a first 3D model image of the patient dentition and obtaining a segmentation of the first 3D model image, wherein the segmentation provides at least a tooth surface contour and a tooth label for at least one tooth of the first 3D model image; (ii) obtaining a second 3D model image of the patient dentition, the second 3D model image having a surface; (iii) registering each segmented tooth surface contour of the first 3D model image to the surface of the second 3D model image; (iv) obtaining a second segmentation of the second 3D model image according to the registered tooth surface contour, wherein the second segmentation similarly provides at least tooth surface contour and tooth labeling for at least one tooth of the second 3D model image; and c) a display that is in signal communication with the processor for displaying the segmented second 3D model image.

* * * * *

UNITED STATES PATENT AND TRADEMARK OFFICE
CERTIFICATE OF CORRECTION

PATENT NO. : 11,961,238 B2  
APPLICATION NO. : 17/418634  
DATED : April 16, 2024  
INVENTOR(S) : Delphine Reynard et al.

Page 1 of 1

It is certified that error appears in the above-identified patent and that said Letters Patent is hereby corrected as shown below:

On the Title Page

Item [30], Line 1, delete "(FR)" and insert -- (EP) --, therefor.

In the Claims

In Column 12, Line 43, Claim 15, delete "3-Diniensional" and insert -- 3- Dimensional --, therefor.

Signed and Sealed this
Eighth Day of October, 2024

Katherine Kelly Vidal
*Director of the United States Patent and Trademark Office*